(12) United States Patent
Groβ et al.

(10) Patent No.: US 9,289,902 B2
(45) Date of Patent: Mar. 22, 2016

(54) SUPPLY LINE ARRANGEMENT FOR A ROBOT

(75) Inventors: Stefan Groβ, Trabitz (DE); Harald Neumann, Parkstein (DE); Franz Schmeisser, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 125 days.

(21) Appl. No.: 12/889,024

(22) Filed: Sep. 23, 2010

(65) Prior Publication Data
US 2011/0072931 A1 Mar. 31, 2011

(30) Foreign Application Priority Data
Sep. 29, 2009 (DE) .......................... 10 2009 043 448

(51) Int. Cl.
B25J 18/00 (2006.01)
B25J 19/00 (2006.01)
A61B 6/00 (2006.01)
H02G 11/02 (2006.01)

(52) U.S. Cl.
CPC ........... *B25J 19/0025* (2013.01); *A61B 6/4458* (2013.01); *A61B 6/56* (2013.01); *H02G 11/02* (2013.01); *Y10T 74/20311* (2015.01)

(58) Field of Classification Search
CPC .......... B25J 19/0025; B25J 18/06; B25J 9/12; B65H 75/4484; B65H 75/4486; B65H 75/4402; B65H 75/38; B65H 75/4436; B65H 75/4471; B60S 5/04; B64D 39/02; A01K 89/015; A47L 9/26; H02G 11/02
USPC ........ 74/490.01, 490.02; 901/50; 137/355.12, 137/355.19, 355.2, 355.21, 355.22, 355.23, 137/899.1; 242/178, 223, 225, 226, 249, 242/250, 251, 255, 287, 397, 397.1, 397.5, 242/370, 371, 399, 399.1; 254/264; 362/358; 378/194, 62; 119/794, 795; 600/424
See application file for complete search history.

(56) References Cited

U.S. PATENT DOCUMENTS 1,950,833 A * 3/1934 Woodford ..................... 242/377
3,207,451 A * 9/1965 Kane .......................... 242/390.9
(Continued)

FOREIGN PATENT DOCUMENTS

DE 40 18 435 A1 12/1991
DE 196 45 413 A1 10/1997
(Continued)

OTHER PUBLICATIONS

German Office Action dated Jun. 13, 2013 for corresponding German Patent Application No. DE 10 2009 043 448.8 with English translation.

*Primary Examiner* — William Kelleher
*Assistant Examiner* — Thomas Magnuson
(74) *Attorney, Agent, or Firm* — Lempia Summerfield Katz LLC

(57) ABSTRACT

An arrangement includes a robot having a robot arm that supports a device powered by supply lines. The arrangement includes at least one guide element that is fastened to the robot arm, and the supply lines are moveably held against at least one segment of the robot arm by the at least one guide element. At least one storage element is provided for receiving a supply line provision. The at least one storage element releases the supply line from the supply line provision with an increasing tensile load of the supply lines and retracts the supply line into the supply line provision with a decreasing tensile load of the supply lines.

15 Claims, 4 Drawing Sheets

(56) References Cited

U.S. PATENT DOCUMENTS

| | | | | |
|---|---|---|---|---|
| 3,543,989 | A | * | 12/1970 | Cooper .................. 228/25 |
| 3,674,049 | A | * | 7/1972 | Macgregor .............. 137/355.2 |
| 3,913,756 | A | * | 10/1975 | Barron et al. ............ 414/586 |
| 4,499,341 | A | * | 2/1985 | Boyd ...................... 191/12.4 |
| 4,507,042 | A | * | 3/1985 | Suzuki et al. ............ 414/680 |
| 4,529,352 | A | * | 7/1985 | Suzuki et al. ............ 414/680 |
| 4,705,243 | A | * | 11/1987 | Hartmann et al. ........ 248/51 |
| 5,088,873 | A | * | 2/1992 | Ruder et al. ............. 414/392 |
| 5,450,466 | A | * | 9/1995 | Kadowaki et al. ........ 378/194 |
| 5,495,995 | A | * | 3/1996 | Dominique et al. ...... 242/390.1 |
| 5,498,940 | A | * | 3/1996 | Kim et al. ................. 318/6 |
| 5,678,596 | A | * | 10/1997 | Corallo .................... 137/357 |
| 5,829,307 | A | | 11/1998 | Harima et al. |
| 6,149,096 | A | * | 11/2000 | Hartley .................... 242/390.9 |
| 6,293,504 | B1 | * | 9/2001 | Hartmann ................. 248/74.1 |
| 6,431,018 | B1 | * | 8/2002 | Okada et al. ............. 74/490.02 |
| 6,543,307 | B2 | * | 4/2003 | Ambrose .................. 74/490.03 |
| 6,669,135 | B1 | * | 12/2003 | Hartley .................... 242/390.9 |
| 6,811,124 | B2 | * | 11/2004 | Karlinger ................. 248/49 |
| 7,334,601 | B1 | * | 2/2008 | Torkelson ................. 137/355.2 |
| 7,520,473 | B2 | | 4/2009 | Karlinger |
| 7,810,765 | B2 | * | 10/2010 | Burlot ...................... 248/75 |
| 8,051,741 | B2 | * | 11/2011 | Inoue et al. ............... 74/490.01 |
| 2004/0261562 | A1 | * | 12/2004 | Haniya et al. ............. 74/490.02 |
| 2007/0158504 | A1 | * | 7/2007 | Burlot ...................... 248/52 |
| 2008/0033417 | A1 | * | 2/2008 | Nields et al. ............. 606/27 |
| 2008/0164361 | A1 | * | 7/2008 | Fancher .................... 242/381 |
| 2008/0164363 | A1 | * | 7/2008 | Caamano et al. ......... 242/390.2 |
| 2008/0236324 | A1 | * | 10/2008 | Inoue et al. ............... 74/490.02 |
| 2008/0247516 | A1 | * | 10/2008 | Fink et al. ................. 378/194 |
| 2008/0271561 | A1 | * | 11/2008 | Ohara et al. .............. 74/490.01 |
| 2009/0127370 | A1 | * | 5/2009 | Brown ...................... 242/397.2 |
| 2010/0270521 | A1 | * | 10/2010 | Hock et al. ............... 254/264 |
| 2011/0067519 | A1 | * | 3/2011 | Graham et al. ........... 74/490.04 |
| 2011/0072931 | A1 | * | 3/2011 | Gro et al. ................. 74/490.02 |
| 2011/0209383 | A1 | * | 9/2011 | Tennyson ................. 43/21 |
| 2012/0000312 | A1 | * | 1/2012 | Collmer .................... 74/490.06 |

FOREIGN PATENT DOCUMENTS

| | | | |
|---|---|---|---|
| DE | 10 2004 019 838 A1 | 11/2005 | |
| DE | 10 2006 002 637 A1 | 8/2007 | |
| DE | 10 2007 018 543 A1 | 10/2008 | |
| DE | 10 2007 058 990 A1 | 6/2009 | |
| DE | 10 2008 011 383 A1 | 9/2009 | |
| DE | 20 2006 020 825 U1 | 7/2010 | |
| JP | 04013593 A * | 1/1992 | ............ B25J 19/00 |
| WO | WO 2008/125093 A2 | 10/2008 | |
| WO | WO 2009/106332 A1 | 9/2009 | |

* cited by examiner

SUPPLY LINE ARRANGEMENT FOR A ROBOT

This application claims the benefit of DE 10 2009 043 448.8, filed Sep. 29, 2009.

BACKGROUND

The present embodiments relate to an arrangement having a robot including a robot arm that supports a device powered by supply lines.

One general problem in robots within the industrial and medical technology fields arises if a device supported by a robot arm is powered by a larger number of electrical, hydraulic, pneumatic and/or other supply lines. The supply lines may not be guided within the robot arm since corresponding moveable pins would be used for each supply line in each joint of the robot arm. The supply lines may therefore be guided to the device outside of the robot arm. To protect the supply lines from damage, the supply lines may be guided in a tube. Flexible tubes may be used herefor, since flexible tubes possess high flexibility in all directions in the case of high rigidity.

A line and/or tube provision is provided so that the mobility of the arrangement is not restricted. The line or tube guidance takes place such that the tube and the supply lines running in the tube are not damaged during movement of the robot arm and of the device supported by the robot and that the tube following the movements of the robot arm with an inertia-dependent delay does not cause damage to other components.

An arrangement is known from the patent application DE 10 2007 058 990 A1, whereby the supply lines are guided to the device from above. The supply lines are arranged on a gallows that is rotatably mounted on a rail-guided carriage and are suspended on a longitudinal section using at least one cable pull on the gallows side.

In other words, in accordance with DE 10 2007 058 990 A1, the tube provision is guided as close as possible to the device position by carriages and rotatable gallows. For movements of the device, which is detached using one or several cable pulls since the carriages and gallows of the device are not able to follow, the tube reserve may be available and released if necessary. This relates to device movements in the vertical direction and device movements on the outermost horizontal boundaries of the operating space.

The arrangement according to DE 10 2007 058 990 A1 is problematical in two respects. The design, including rail system, carriage and gallows, is mechanically complicated, and the tube and robot arm may collide.

SUMMARY AND DESCRIPTION

The present embodiments may obviate one or more of the drawbacks or limitations in the art. For example, an arrangement that is mechanically less complicated may be specified.

One embodiment of an arrangement includes at least one guide element that is fastened to a robot arm. Using the at least one guide element, the supply lines are moveably held against at least one segment of the robot arm. The arrangement includes at least one storage element for receiving the supply line provision, the storage element releasing the supply line from the supply line provision when there is an increase in the tensile load of the supply lines and retracting the supply line into the supply line provision with a reducing tensile load of the supply lines.

In one embodiment, a spring-loaded wheel is used as the storage element. The supply line or tube provision may be stored on an outer diameter of the spring-loaded wheel. An energy chain, which may be a chain link guide, may be arranged in the inside of the wheel, the energy chain balancing out the rotational movement of the supply lines or the tube. The storage element may be arranged directly on the robot or ceiling mounted in the vicinity of the robot.

The at least one guide element may be rotatably mounted and/or hinged.

In one embodiment, a rotatable and/or hinged supply line inlet may be provided on the device.

One advantage of the present embodiments may be that only the least necessary supply line length and/or tube length exists and is free and only short paths exist, along which the line proceeds unguided. As a result, a loose suspension of the tube is prevented and robot movements may not result in collisions between the tube and robot. Furthermore, no complicated rail constructions, significantly fewer components and in particular far fewer moveable components are needed than in known solutions.

DETAILED DESCRIPTION OF THE DRAWINGS

Figure 1A:
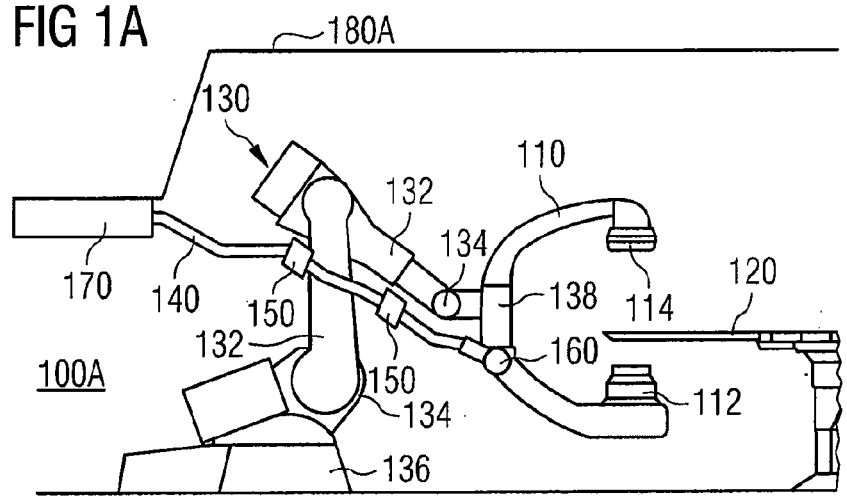
FIGS. 1A-1C show embodiments of an arrangement with three different assembly sites of a storage element.
Figure 1B:
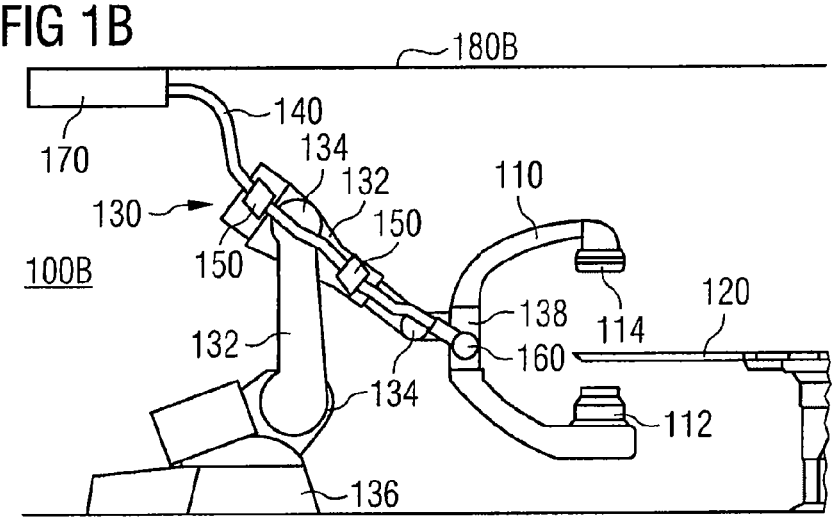
Figure 1C:
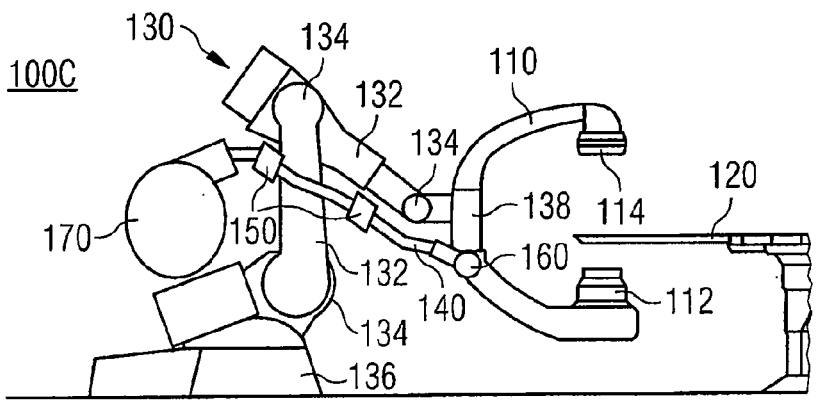

FIGS. 1A-1C show embodiments of an arrangement (e.g., a system) 100A, 100B and 100C that, by way of example, involve medical x-ray examination systems in each case. As the arrangements 100A-C differ in terms of a few details, the arrangements 100A-C are explained below with reference to FIGS. 1A-C.

The x-ray examination systems 100 shown in FIGS. 1A-C include a C-arm 110 with a radiation source 112 and an x-ray detector 114. The x-ray examination system 100 also includes a patient support couch 120, on which a patient is to be arranged for examination. The C-arm 110 is arranged on a robot arm 130 in the embodiments shown. The robot arm 130 includes a plurality of arm sections 132 that are connected to one another by at least one swivel joint 134. An arm section 132 of the plurality is connected to the C-arm 110 by a swivel joint 134, and another arm section 132 of the plurality is connected to a robot stand 136 by another swivel joint 134. The robot arm 130 is rotatably moveable about a vertical axis. The C-arm 110 may also be moved along the arc form of the C-arm 110 and may be rotated about the longitudinal axis of a robot hand 138 supporting the C-arm. The different degrees of freedom of movement allow for the x-ray diagnostic examination of each body part of the patient along each arbitrary imaging axis. The movement of the robot arm 130 is controlled by a controller (not shown) of the robot.

Devices (e.g., the radiation source 112 and the x-ray detector 114) arranged on the C-arm 110 are powered by supply lines (not shown) that are guided in a tube 140 to the C-arm 110 to bundle the supply lines and protect against external influences and damages.

Figure 3:
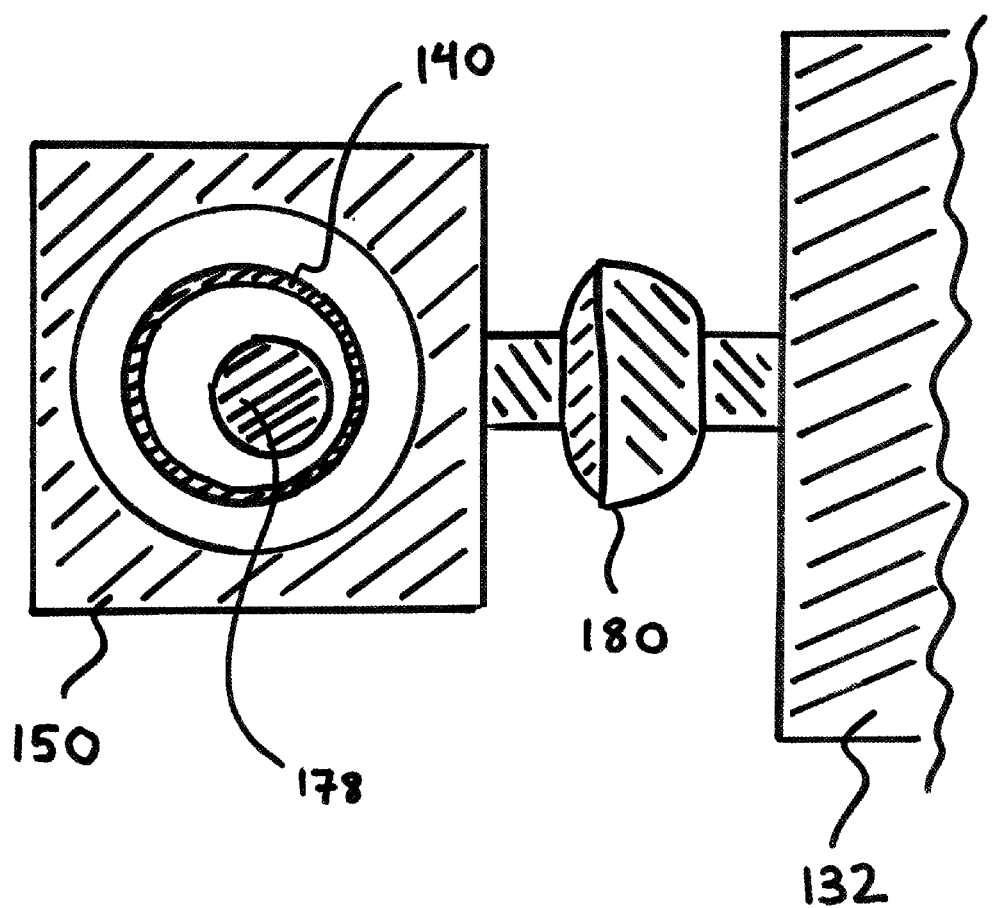
FIG. 3 shows a cross-sectional view of an embodiment of a rotatably mounted and/or hinged guide element.

The tube 140 is guided by guide elements 150 along an arm section 132 and is held by the guide elements 150 close to the arm section 132, so that the arm section 132 and the corresponding tube section execute corresponding movements, and collisions cannot occur. In one embodiment, the guide elements 150 are designed such that the tube may slide in the longitudinal direction using the guide elements 150 if, as a result of a movement of the robot hand 138 or the C-arm 110, an additional tube is needed or released again. The guide elements 150 may be rotatably mounted and/or hinged on a spherical joint with a boundary collar to, for example, enable an alignment of the guide elements 150 along a tube clamping direction. This prevents the tube 140 from buckling too significantly on the guide elements 150. FIG. 3 shows a cross-sectional view of the guide element 150 rotatably mounted and/or hinged to the arm section 132 through a spherical joint 180.

The tube 140 ends at the C-arm 110 in a rotatable and/or hinged supply line inlet 160. From the supply line inlet 160, the supply lines may be guided within the rigid C-arm 110 to the devices 112 and 114. If the C-arm 110 is moved along the arched shape of the C-arm 110 or rotated by the robot hand 138, the tube 140 winds around the robot hand by the shortest route. Therefore, the tube 140 touches the robot but does not collide with the robot in the sense that a tube oscillating loosely as a result of, for example, inertia, uncontrollably strikes the robot arm 130 moving in the opposite direction or moving slowly.

Another end of the tube 140 is located in a storage element 170 that receives and, if necessary, releases the tube provision alongside the supply line provision (e.g., stored tube and supply line) used for the freedom of movement. The storage element 170 releases the tube 140 if the tensile load of the tube 140 increases as a result of a movement of the robot arm 130, and retracts the tube 140 again, if the tensile load of the tube 140 reduces as a result of a movement of the robot arm 130.

The release and retraction of the tube 140 may take place, for example, using a motor-controlled wheel that applies a counteracting force on the tube 140 to constantly keep the tube 140 taut. If the tensile force exceeds a predetermined first value, the tube 140 is unwound from the wheel in a controlled fashion. If the tensile force does not reach a second value, the tube 140 is wound onto the wheel.

It is sufficient in many cases to select the predetermined first value (at least approximately) to equate to the second value and to select a uniform threshold value for tube release and retraction purposes.

FIGS. 1A-C show different variants with respect to the arrangement of the storage element 170, the guide elements 150 and the supply line inlet 160.

In the embodiments shown in FIG. 1A, the guide elements 150 and the supply line inlet 160 are arranged below the arm section 132 attached to the C-arm 110, and the storage element 170 is mounted on a lower section of a ceiling 180A. As a result, this produces a tube course below the arm section 132 attached to the C-arm 110.

In the embodiment shown in FIG. 1B, the guide elements 150 are arranged laterally on the arm section 132 attached to the C-arm 110. The supply line inlet 160 is located approximately centrally on the C-arm 110, and the storage element 170 is mounted on a ceiling 180B at a conventional height. As a result, a tube course is produced laterally adjacent to the arm section 132 attached to the C-arm 110.

In the embodiment shown in FIG. 1C, the guide elements 150 and the supply line inlet 160 are arranged below the arm section 132 attached to the C-arm 110, and the storage element 170 is mounted on the robot stand 136. As a result, a tube course is produced below the arm section 132 attached to the C-arm 110. This arrangement is advantageous in that the storage element 170 is rotated with the robot arm 130 about the vertical axis, and the tube 140 is, as a result, under less stress.

Figure 2:
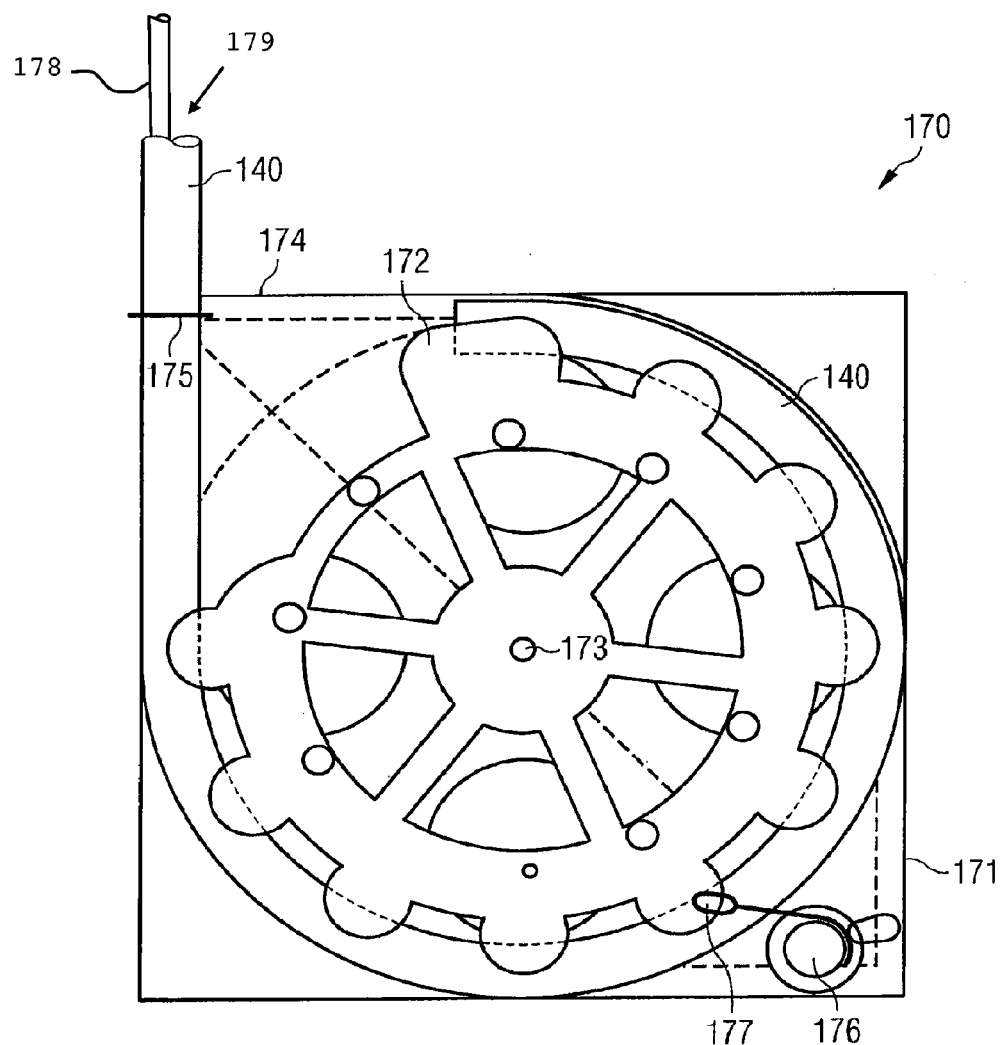
FIG. 2 shows one embodiment of a storage element.

FIG. 2 shows a top view of one embodiment of a storage element 170 with an opened housing 171. A portion of the storage element 170—namely, the housing 171—is fixedly mounted to a mounting surface (e.g., ceiling 180A in FIG. 1A, ceiling 180B in FIG. 1B, or robot stand 136 in FIG. 1C), and does not move relative to the mounting surface. The housing 171 of the storage element 170 contains a wheel 172, shown with six spokes, that is rotatably mounted about an axis 173 and supports the tube 140. The tube 140 leaves the storage element 170 at an opening 174. As shown in FIG. 2, a supply line provision 179 runs through the tube 140. For simplicity, a single supply line 178 is shown in FIG. 2 although a plurality of supply lines may be provided.

A tube guide 175 that restricts the tube exit to a single point or allows for the tube exit over a certain width in order to enable exit of the tube at different angles (not shown) may be provided.

In the embodiment shown in FIG. 2, the wheel 172 is designed such that approximately three quarters of the periphery of the wheel 172 is sufficient to receive the tube provision in addition to the supply line provision so that the wheel does not execute more than a three quarter rotation when releasing or retracting the tube.

Figure 4:
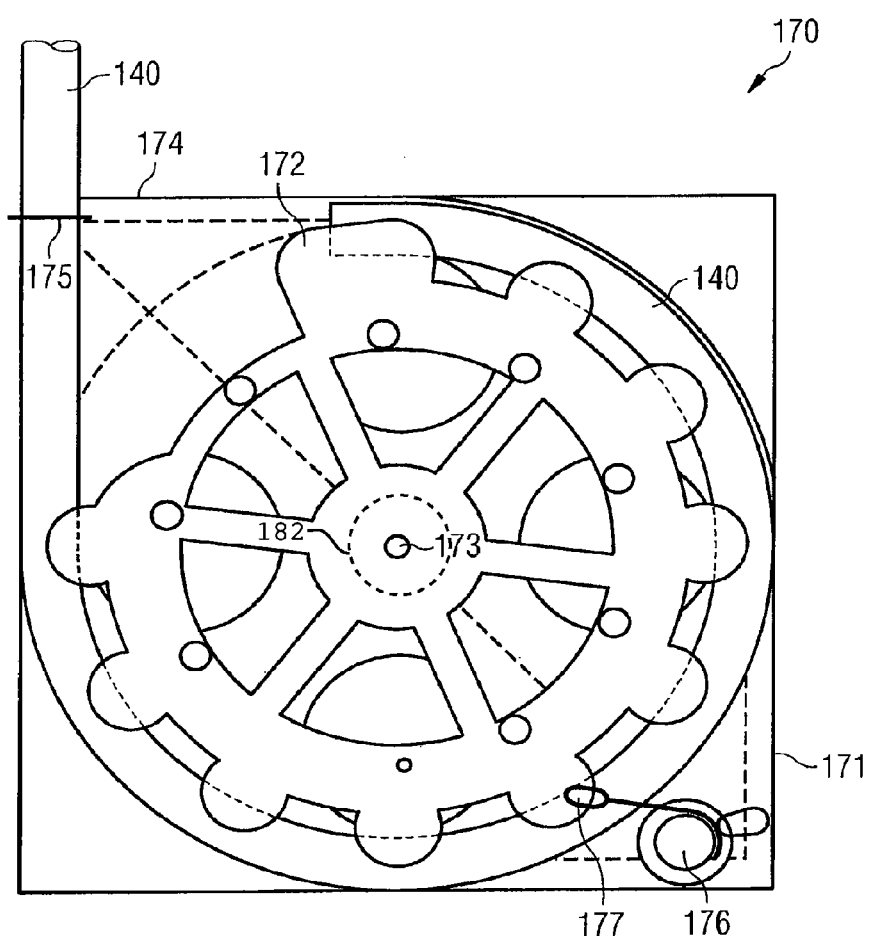
FIG. 4 shows one embodiment of a storage element.

In one embodiment, the wheel 172 is spring loaded (e.g., a movement of the tube 140 out of the storage element 170 results in a spring being tensioned, which then effects the force that retracts the tube again). As shown in FIG. 4, a screw or a spiral spring 182 may be provided concentrically to the axis 173, for example, or a spring balancer 176 engages at a point 177 of the wheel and effects the force that retracts the tube again.

An energy chain may be provided inside the storage apparatus 170 in order to balance out the rotational movement of the supply lines and/or the tube 140 (not shown).

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A system comprising:
    a robot comprising:
        a robot arm comprising a plurality of arm sections, each arm section connected to an adjacent arm section by a swivel joint, wherein the robot arm supports a device powered by supply lines extending through a tube;
        a plurality of guide elements, each guide element of the plurality of guide elements being externally fastened to the robot arm and being rotatably mounted, hinged, or rotatably mounted and hinged, the tube being moveably held on an external surface of a segment of the robot arm with the plurality of guide elements; and
        a storage element fixedly mounted to a mounting surface, such that at least a portion of the storage element does not move relative to the mounting surface, wherein the storage element is configured to receive a tube provision, wherein a supply line provision runs in the tube provision, wherein the storage element is operable to release the tube from the tube provision with an increasing tensile load of the tube and retract the tube into the tube provision with a decreasing tensile load of the tube, wherein the storage element comprises a wheel that supports the tube provision, wherein the wheel is configured to rotate less than a full rotation when the tube is released from the tube provision and when the tube is retracted into the tube provision, and wherein the tube is slidable along the plurality of guide elements, such that the wheel is operable to apply a counteracting force on the tube to keep the tube taut along the external surface of the robot arm.

2. The system as claimed in claim 1, wherein the wheel is a spring-loaded wheel.

3. The system as claimed in claim 2, wherein the tube is stored on an outer diameter of the spring-loaded wheel.

4. The system as claimed in claim 1, wherein the storage element is arranged directly on the robot or is ceiling mounted in the vicinity of the robot.

5. The system as claimed in claim 1, wherein the robot comprises a rotatable, hinged, or rotatable and hinged supply line inlet.

6. The system as claimed in claim 2, wherein the storage element is arranged directly on the robot or is ceiling mounted in the vicinity of the robot.

7. The system as claimed in claim 3, wherein the storage element is arranged directly on the robot or is ceiling mounted in the vicinity of the robot.

8. The system as claimed in claim 2, wherein the robot comprises a rotatable, hinged, or rotatable and hinged supply line inlet.

9. The system as claimed in claim 3, wherein the robot comprises a rotatable, hinged, or rotatable and hinged supply line inlet.

10. The system as claimed in claim 4, wherein the robot comprises a rotatable, hinged, or rotatable and hinged supply line inlet.

11. A system comprising:
    a robot comprising:
        a robot arm comprising a plurality of arm sections, each arm section connected to an adjacent arm section by a swivel joint, wherein the robot arm supports a device powered by supply lines;
        a plurality of guide elements, each guide element of the plurality of guide elements being externally fastened to the robot arm and being rotatably mounted, hinged, or rotatably mounted and hinged, the supply lines being moveably held on an external surface of a segment of the robot arm with the plurality of guide elements; and
    a storage element fixedly mounted to a mounting surface, such that at least a portion of the storage element does not move relative to the mounting surface, wherein the storage element is configured to receive a supply line provision, wherein the storage element is operable to release the supply lines from the supply line provision with an increasing tensile load of the supply lines and retract the supply lines into the supply line provision with a decreasing tensile load of the supply lines, wherein the storage element comprises a wheel that supports the supply line provision, wherein the wheel is configured to rotate less than a full rotation when the supply lines are released from the supply line provision and when the supply lines are retracted into the supply line provision, and wherein the supply lines are slidable along the plurality of guide elements, such that the wheel is operable to apply a counteracting force on the supply lines to keep the supply lines taut along the external surface of the robot arm.

12. The system as claimed in claim 11, wherein the supply lines run in a tube, and
    wherein the motor-controlled wheel is operable to unwind the tube from the motor-controlled wheel when a tensile force on the tube exceeds a predetermined value.

13. The system as claimed in claim 12, wherein the predetermined value is a first predetermined value, and
    wherein the motor-controlled wheel is operable to wind the tube onto the motor-controlled wheel when the tensile force on the tube is less than a second predetermined value.

14. The system as claimed in claim 1, wherein the storage element further comprises a housing in which the wheel is positioned, the housing of the storage element being fixedly mounted to the mounting surface.

15. The system as claimed in claim 1, wherein the device is a C-arm device.

* * * * *